United States Patent [19]

Hasegawa et al.

[11] Patent Number: 5,407,973

[45] Date of Patent: Apr. 18, 1995

[54] DENTAL COLD-POLYMERIZING RESIN COMPOSITION

[75] Inventors: Akira Hasegawa, Inuyama; Makoto Katsu, Yamaoka, both of Japan

[73] Assignee: GC Dental Products Corp., Kasugai, Japan

[21] Appl. No.: 132,818

[22] Filed: Oct. 7, 1993

[30] Foreign Application Priority Data

Jan. 25, 1993 [JP] Japan .................................. 5-027110

[51] Int. Cl.⁶ ............................ A61K 6/08; C08F 4/06
[52] U.S. Cl. .................................... 523/116; 526/135; 526/147; 526/192; 526/204
[58] Field of Search ................ 523/116; 526/135, 147, 526/192, 204, 217, 141

[56] References Cited

U.S. PATENT DOCUMENTS 4,880,887 11/1989 Hasegawa ......................... 526/141
5,250,641 10/1993 Kumagai et al. .................. 526/141

*Primary Examiner*—Paul R. Michl
*Assistant Examiner*—LaVonda DeWitt
*Attorney, Agent, or Firm*—Oblon, Spivak, McClelland, Maier & Neustadt

[57] ABSTRACT

In a powder-liquid type of dental cold-polymerizing resin composition, the powder component comprises a specific polymer such as polymethylmethacrylate containing a pyrimidinetrione derivative and an organometallic compound mixed at a specific proportion, and the liquid component comprises a radical polymerizable compound containing an organic halogen compound and an aromatic tertiary amine mixed at a specific proportion used with a polymerization inhibitor.

8 Claims, 2 Drawing Sheets

DENTAL COLD-POLYMERIZING RESIN COMPOSITION

BACKGROUND OF THE INVENTION

The present invention relates to dental cold-polymerizing resin, and particularly to a dental resin composition that is much more improved in terms of color stability and curing properties. More particularly, care is taken of using a powder-liquid type of cold-polymerizing resin by brush on technic.

Even at the present time, the cold (or normal temperature) polymerization of methyl methacrylate, etc., with organic peroxides and aromatic tertiary amines finds wide application in dentistry. To a lesser extent, the cold polymerization of methyl methacrylate, etc., with pyrimidinetrione derivatives and organometallic compounds and optionally with organic halogen compounds is applied to some products.

These dental cold-polymerizing resins are widely and diversely used as temporary crowns that are temporary substitutes for permanent crown prostheses or bridges, for repairing broken denture base or artificial teeth, and for other purposes. Generally, they are used by a technical procedure called "brush on technic". According to this "brush on technic", the tip of a small brush made up of swine or nylon bristles is first impregnated with a sufficient amount of liquid material, and then brought into contact with powder materials. The liquid incorporated in the brush enters among the powder particles forming the powder material through capillarity. As the powder comes into contact with the liquid or is mixed with the liquid, they start to react with each other. The behavior of the polymerization achieved by this procedure is considerably different from that achieved by mixing together constant amounts of the powder and liquid materials in a rubber cup with the use of a spatula or other means. This can be well understood by measuring a (approx. 0.1-0.5 g) scoop of material taken up by brush on technic for curing capability. In other words, the scoop of material is inhomogeneously cured. This phenomenon has been common to both the reaction in which organic peroxide and aromatic tertiary amine compounds participate and that in which pyrimidinetrione derivative, organometallic and organic halogen compounds participate, and has offered some difficulty, although it has been somehow averted by skillful dentists or dental technicians.

The reaction in which the pyrimidinetrione derivative, organometallic and organic halogen compounds participate yields a cured material that does not suffer from yellowing, but the reaction in which the organic peroxide and aromatic tertiary amine compounds participate yields a cured material that tends to suffer from yellowing. However, this yellowing problem is still .considered very difficult to solve technically, and so is left as it is.

Another problem with brush on technic is that air bubbles are likely to enter the cured material and, after polishing, remains in the form of impurity. Moreover, the air bubbles may act as a certain type of defects, and cause a drop in mechanical strength, which may lead to a re-fracture.

Thus, problems in connection with inhomogeneous curing caused by brush on technic, yellowing of cured material, and air bubbles brought about by brush on technic all remain unsolved.

The brush on technic of a conventional powder-liquid type of cold-polymerizing resin making use of the reaction in which organic peroxide and aromatic tertiary amine compounds participate and the reaction in which pyrimidinetrione derivative, organometallic and organic halogen compounds participate have the following problems.

1. Brush on technic makes curing inhomogeneous

Now consider a (approx. 0.1-0.5 g) scoop of material taken up by brush on technic. The capability of this scoop of material to cure can be estimated by measuring the curing time in a regulated-temperature room of 23° C. by a contact procedure making use of a Vicat needle with a sectional area of 1 mm$^2$. There is some considerable difference in the curing time between the outer and central surface portions of a scoop. Here consider a commercially available material (e.g., GC UNIFAST) containing an organic peroxide and an aromatic tertiary amine. The outer surface portion of a scoop of this material is generally cured for about 4 minutes at 23° C. However, a considerable longer time that is about 10 minutes to about 20 minutes is needed to cure the central portion of a scoop.

Then, consider a scoop of an experimental material composed of a pyrimidinetrione derivative, an organometallic compound and an organic halogen compound under the same conditions. The outer surface portion of the experimental material is cured very sharply or for a short time in a matter of 3 minutes at 23° C., but the central portion thereof is not cured at all.

Thus, when such inhomogeneous curing happens, it takes much time for dentists or dental technicians to make temporary crowns or repair broken denture base or artificial teeth, resulting in an increase in the time taken by dentists for dental examination and treatment and in the time needed for dental technicians works. One scoop of material starts to be cured on its outer surface, and when the material is polished at this time, the uncured central portion of the material is wound round the polishing bar, leaving white stripes. These pose an aesthetic problem in the case of temporary crowns or repaired denture base or artificial teeth; it is required to redo dental examination and treatment or dental works.

2. Yellowing of cured material

As mentioned, the cold polymerization of a radical polymerizable compound having at least one ethylenically unsaturated double bond (e.g., methyl methacrylate) by the reaction in which an organic peroxide and an aromatic tertiary amine participate yields a cured material that suffers from yellowing when the polymerization is achieved by any one of the procedures of brush on technic or mixing. This problem is known to be solved by use of a combination of three catalysts, i.e., a pyrimidinetrione derivative, an organometallic compound and an organic halogen compound, as disclosed in Japanese Patent Application No. 62-50295, entitled "Method for Curing of Dental Resin". In the case of the brush on technic, however, it is required to solve the inhomogeneous curing and yellowing problems at the same time. Never until now is there any powder-liquid type of dental cold-polymerizing resin capable of solving the inhomogeneous curing-upon-brush on technic and yellowing problems at the same time.

3. Internal air bubbles are generated when the brush on technic is used

Except when polymerized in a pressure vessel, catalysts, e.g., an organic peroxide and an aromatic tertiary amine, when used for the cold polymerization of a radical polymerizable compound having at least one ethylenically unsaturated double bond (e.g., methyl methacrylate), causes the reaction to proceed too rapidly, resulting in the generation of some considerable internal air bubbles upon brush on technic. This poses a problem when temporary crowns are polished on their surfaces or broken denture base or artificial teeth are polished on their surface after repairing, because impurity upon polishing remains in these air bubbles. The air bubbles makes the resin inferior in the mechanical strength and so causes a re-fracture, because the resin cannot produce its own properties.

SUMMARY OF THE INVENTION

According to the invention, there is provided a powder-liquid type of dental cold-polymerizing resin composition composed of powder and liquid components that are brought in contact with each other and mixed together for curing, said powder component comprising:

(A) no added benzoyl peroxide homopolymer of polymethacrylate ester and/or no added benzoyl peroxide copolymer of polymethacrylate ester, (B) pyrimidinetrione derivative in an amount lying in the range of 0.05 to 5% by weight per 100 parts by weight of the polymer (A), and (C) an organometallic compound in an amount lying in the range of 0.0005 to 0.1 parts by weight per 100 parts by weight of the polymer (A), and said liquid component comprising:

(D) a radical polymerizable compound having at least one ethylenically unsaturated double bond, (E) an organic halogen compound in an amount lying in the range of 0.1 to 5 parts by weight per 100 parts by weight of the compound (D), (F) an aromatic tertiary amine in an amount lying in the range of 0.1 to 5 parts by weight per 100 parts by weight of the compound (D), and (G) a polymerization inhibitor.

When the resin composition of the invention is used for temporary crowns that are temporary substitutes for permanent crown prostheses or bridges, or for repairing broken denture base or artificial teeth, 1 ml of the liquid component is typically used per 2 g of the powder component, and they are mixed together by the brush on technic for polymerization to obtain a cured material.

As noted, the major cause of yellowing is the reaction of benzoyl peroxide with the aromatic tertiary amine. In the invention, however, no yellowing takes place, because the powder component contains no benzoyl peroxide. In this connection, it is noted that when curing is done with a system comprising a liquid component consisting only of an aromatic tertiary amine and a powder component not containing all three catalysts, i.e., benzoyl peroxide, a pyrimidinetrione derivative and an organometallic compound, no yellowing occurs but an extremely long time span of a few hours is needed for curing. With a system comprising a powder component free from benzoyl peroxide and containing only two catalysts, i.e., a pyrimidinetrione derivative and an organometallic compound and a liquid component consisting only of an organic halogen compound, curing becomes inhomogeneous.

In the invention, therefore, it is essentially important that two catalysts, i.e., the pyrimidinetrione derivative and organometallic compound be incorporated in the powder component and two catalysts, i.e., the organic halogen compound and aromatic tertiary amine be included in the liquid component; in other words, the system contains a total of four catalysts.

All the three problems mentioned above can be well solved by the brush on technic of the system according to the invention. More specifically, the inhomogeneous curing upon brush on technic is eliminated by the aromatic tertiary amine contained in the liquid component, no yellowing of the cured material takes place in the absence of benzoyl peroxide, and no generation of the internal air bubbles upon brush on technic takes place, because the reaction in which the four catalysts mentioned above participate is more moderate than that in which benzoyl peroxide and the aromatic tertiary amine participate, and these are major reasons for a successful solution of all the three problems mentioned above by the invention.

Figure 1:
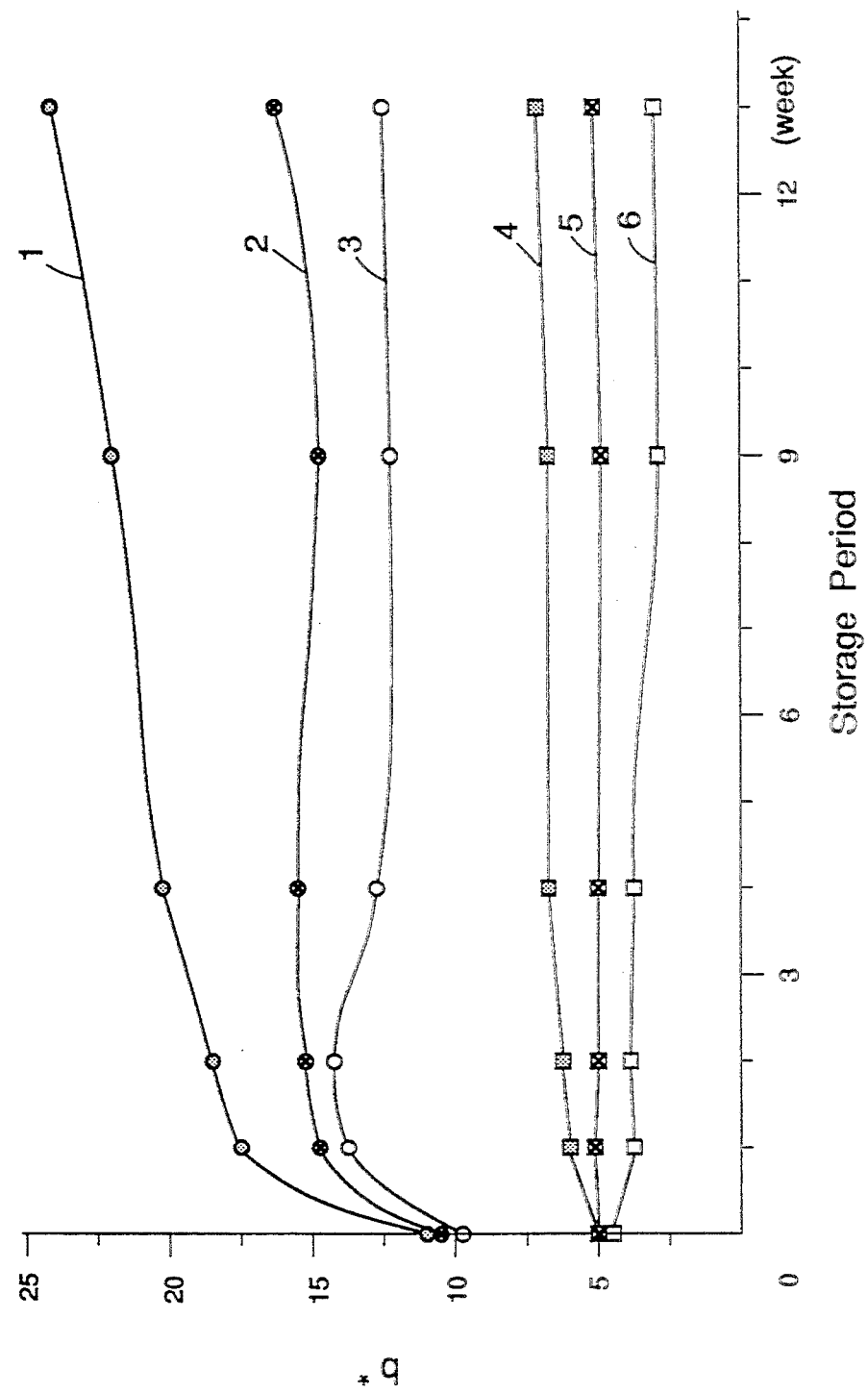
FIG. 1 represents the degrees of yellowing "b*" of the cured resin materials obtained in Example 1 and Comparative Example 9.

In the present disclosure, the term "no added benzoyl peroxide homopolymer and/or copolymer of polymethacrylate ester" is understood to refer to a spherical or other like form of powder obtained by suspension polymerization, to which benzoyl peroxide is not added at any later stage. By way of example alone and not by way of limitation, polymethyl methacrylate, polyethyl methacrylate, polybutyl methacrylate, polyisobutyl methacrylate, methyl ethyl methacrylate copolymer, butyl isobutyl methacrylate copolymer, methyl methacrylate styrene copolymer and a crosslinked type polymethyl methacrylate are mentioned. These polymers may be used alone or in combination of two or more.

The pyrimidinetrione derivative used, for instance, include N-cyclohexyl 5-ethylpyrimidinetrione, 1-benzyl 5-phenylpyrimidinetrione, 5-butylpyrimidinetrione, 5-phenylpyrimidinetrione, 1,3-dimethylpyrimidinetrione, and 5-ethylpyrimidinetrione. Among these, particular preference is given to N-cyclohexyl 5-ethylpyrimidinetrione. However, these pyrimidinetrione derivatives may be used alone or in combination of two or more.

Preferably, the pyrimidinetrione derivative is used in an amount of 0.05 to 5 parts by weight per 100 parts by weight of the no added benzoyl peroxide homopolymer and/or copolymer of polymethacrylate ester. At less than 0.05 parts by weight and more than 5 parts by weight, the pyrimidinetrione derivative fails to provide any dental cold-polymerizing resin needed to be rapidly cured, since the resultant composition takes much time to cure.

The organometallic compound used, for instance, include acetylacetone copper, copper 4-cyclohexylbutyrate, copper acetate, copper oleate, acetylacetone manganese, manganese naphthenate, octylic acid manganese, acetylacetone cobalt, cobalt naphthenate, acetylacetone lithium, lithium acetate, acetylacetone zinc, zinc naphthenate, acetylacetone nickel, nickel acetate, acetylacetone aluminum, acetylacetone calcium, acetylacetone chromium, acetylacetone iron, sodium naphthenate, and rare earth octoate. Among these, particular preference is given to acetylacetone copper. However, these organometallic compounds may be used alone or in combination of two or more.

Preferably, the organometallic compound is used in an amount of 0.0005 to 0.1 parts by weight per 100 parts by weight of the polymer. If too little organometallic compound is used, it is then impossible to obtain any dental cold-polymerizing resin needed to be rapidly cured, because the resulting composition is poor in reactivity. If too much is used, the cured material shows the color peculiar to the organometallic compound used.

The radical polymerizable compound having at least one ethylenically unsaturated double bond, for instance, include methyl methacrylate, ethyl methacrylate, isopropyl methacrylate, 2-hydroxyethyl methacrylate, tetrahydrofurfuryl methacrylate, glycidyl methacrylate, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, 2,2-bis(-methacryloxyphenyl)propane, 2,2-bis[4-(2-hydroxy-3-methacryloxyphenyl)propane, 2,2-bis(4-methacryloxyethoxyphenyl)propane, 2,2-bis(4-methacryloxy-diethoxyphenyl)propane, 2,2-bis(4-methacryloxypropoxyphenyl) propane, trimetylolpropane trimethacrylate, pentaerythritol trimethacrylate, trimethylolmethane trimethacrylate, pentaerythritol tetramethacrylate, and these acrylates. These may be used alone or in combination of two or more.

The organic halogen compound used, for instance, include dilauryldimethylammoniumchloride, lauryldimethylbenzylammoniumchloride, tetra-n-butylammoniumchloride, trioctylmethylammoniumchloride, benzyldimethylcetylammoniumchloride, and benzyldimethylstearylammoniumchloride, which may be used alone or in combination of two or more.

Preferably, the organic halogen compound is used in an amount of 0.1 to 5 parts by weight per 100 parts by weight of the radical polymerizable compound having at least one ethylenically unsaturated double bond (hereinafter called the radical polymerizable compound). If too little organic halogen compound is used, it is then impossible to obtain any dental cold-polymerizing resin needed to be rapidly cured, because the resulting composition is poor in reactivity. If too much is used, the cured material shows the color peculiar to the organic halogen compound.

By way of example alone but not by way of limitation, the aromatic tertiary amine used may be N,N-di(β-hydroxyethyl)-p-toluidine, N,N-dimethyl-p-toluidine and N,N-di(2-hydroxypropyl)-p-toluidine, which may be used alone or in combination of two or more.

Preferably, the aromatic tertiary amine is used in an amount of 0.1 to 5 parts by weight per 100 parts by weight of the radical polymerizable compound. If too little aromatic tertiary amine is used, inhomogeneous curing noticeably takes place upon brush on technic. If too much is used, the cured material shows the color peculiar to the aromatic tertiary amine.

By way of example alone but not by way of limitation, the polymerization inhibitor may be hydroquinone, butylhydroxy-toluene, hydroquinone monomethyl ether, and 2,6-dimethyl-6-tertiarybutylphenol, which may be used alone or in combination of two or more.

In the invention, the amount of the polymerization inhibitor used relative to the radical polymerizable compound is not particularly critical.

More specifically but not exclusively, the invention will be explained with reference to examples (with the results reported in Table 1) and comparative examples (with the results shown in Table 2).

In the ensuing description, reference will be made to what was measured.

Resin Curing

To make an estimation of whether or not resin curing occurs homogeneously, separate scoops of powder and liquid are placed in separate vessels. First, a brush is well impregnated with the liquid. Then, the brush is brought in contact with the powder, so that the liquid is allowed to enter well among the powder particles. From this state, the reaction starts. At suitable time intervals, a 1-mm$^2$ Vicat needle is allowed to contact the surface of the powder. If the whole of the powder is found to be uniformly cured after the lapse of predetermined time, the curing is then taken as occurring uniformly. If some regions are found to be cured and others to remain soft after the lapse of given time, the curing is then deemed as taking place inhomogeneously. To estimate the color tone of the cured material, a disk form of sample of 50 mm in diameter and 4 mm in thickness is prepared therefrom, and is visually observed under standard light in terms of the degree of yellowing. If the cured sample is not tinged with yellow at all, it is then taken as being colorless and transparent. Otherwise, the cured sample is estimated to be tinged with white, pale blue, pale yellow, yellow, whitish yellow, etc. To estimate the occurrence of internal air bubbles, the brushed material is visually observed while it is irradiated with transmitting light. If there is no air bubble at all, it is then estimated to be bubble-free. If air bubbles are more or less found, it is then estimated to be bubbled. To measure Vicar needle curing time, a precisely weighed 2 g of powder and a precisely weighed 1 ml of liquid are mixed together in a rubber cup to make a disk form of sample of about 25 mm in diameter and about 5 mm in thickness. At suitable time intervals, the Vicat needle is allowed to contact the surface of the sample to measure the time taken for the whole of the sample to cure completely. In this case, notice that the curing takes place uniformly, because brush on technic is not used.

EXAMPLE 1

In this example, a typical composition according to the invention was used. Nothing abnormal was found in terms of the inhomogeneous curing during brushing, the color tone of the cured material and the occurrence of internal air bubbles. The curing time was 2 minutes 45 seconds, and so was best suited for dental cold-polymerizing resin.

EXAMPLES 2 & 3

In Example 2, the N-cyclohexyl 5-ethylpyrimidinetrione was used in an amount close to the critical lower limit defined by the scope of the claims in the invention.

In Example 3, in contrast, the N-cyclohexyl 5-ethylpyrimidinetrione was used in an amount close to the critical upper limit defined by the scope of the claims in the invention.

In either case, it took somewhat longer time for the composition to cure, but the composition could be used as dental cold-polymerizing resin with no difficulty.

EXAMPLE 4

In the instant example, 1-benzyl 5-phenylpyrimidinetrione and acetyl acetone copper were used as the pyrimidinetrione derivative and organometallic compound, respectively, and they were both used in amounts close to the critical lower limits defined by the scope of the claims of the invention. In this case, it took somewhat longer time for the composition to cure, but it could be used as dental cold-polymerizing resin with no difficulty.

EXAMPLE 5

In the instant example, N-cyclohexyl 5-ethyl-pyrimidinetrione and 1-benzyl 5-phenylpyrimidinetrione were used as the pyrimidinetrione derivative and acetyl acetone copper was used as organometallic compound, and they were both used in amounts close to the critical upper limit defined by the scope of the claims of the invention. In this case, it took somewhat shorter time for the composition to cure, it posed no problem in terms of the tone of color and could be used as cold-polymerizing resin with no difficulty.

EXAMPLES 6-9

In Example 6, dilauryldimethylammoniumchloride was used as the organic halogen compound in an amount close to the critical lower limit defined by the scope of the claims of the invention.

In Example 7, dilauryldimethylammoniumchloride was used in an amount close to the critical upper limit defined by the scope of the claims of the invention.

In Example 8, N,N-di($\beta$-hydroxyethyl)-p-toluidine was used as the aromatic tertiary amine in an amount close to the critical lower limit defined by the scope of the claims of the invention.

In Example 9, N,N-di($\beta$-hydroxyethyl)-p-toluidine was used in an amount close to the critical upper limit defined by the scope of the claims of the invention.

These examples were provided to define the scope of the claims of the invention. In each case, the composition could be used as dental cold-polymerizing resin with no difficulty.

COMPARATIVE EXAMPLES 1 & 2

In Comparative Example 1, N-cyclohexyl 5-ethyl-pyrimidinetrione was used in an amount smaller, than the critical lower limit defined by the scope of the claims of the invention.

In Comparative Example 2, N-cyclohexyl 5-ethyl-pyrimidinetrione was used in an amount larger than the critical upper limit defined by the scope of the claims of the invention.

In either case, it took some considerable time for the composition to cure; that is, it could not be used as dental cold-polymerizing resin.

In Comparative Example 2, the cured material was tinged with white under the influence of N-cyclohexyl 5-ethylpyrimidinetrione.

COMPARATIVE EXAMPLES 3 & 4

In Comparative Example 3, acetyl acetone copper was used in an amount smaller than the critical lower limit defined by the scope of the claims of the invention.

In Comparative Example 4, acetyl acetone copper was used in an amount larger than the critical upper limit defined by the scope of the claims of the invention.

If too little acetyl acetone copper is used, it takes longer time for the composition to cure, and if too much is used, the cured material assumes the pale blue color peculiar to acetyl acetone copper.

COMPARATIVE EXAMPLES 5 & 6

In Comparative Example 5, dilauryldimethylammoniumchloride was used in an amount smaller than the critical lower limit defined by the scope of the claims of the invention.

In Comparative Example 6, dilauryldimethylammoniumchloride was used in an amount larger than the critical upper limit defined by the scope of the claims of the invention.

If too little dilauryldimethylammoniumchloride is used, it takes longer time for the composition to cure, and if too much is used, the cured material shows a pale yellow color.

COMPARATIVE EXAMPLES 7 & 8

In Comparative Example 7, N,N-di($\beta$-hydroxyethyl)-p-toluidine was used in an amount smaller than the critical lower limit defined by the scope of the claims of the invention.

In Comparative Example 8, N,N-di($\beta$-hydroxyethyl)-p-toluidine was used in an amount larger than the critical upper limit defined by the scope of the claims of the invention.

If too little N,N-di($\beta$-hydroxyethyl)-p-toluidine is used, the composition cures inhomogeneously upon brushing, and if too much is used, the cured material assumes a pale yellow color.

COMPARATIVE EXAMPLE 9

In the instant example, benzoyl peroxide was used as powder and N,N-di($\beta$-hydroxyethyl)-p-toluidine as liquid, without using the pyrimidinetrione derivative, organometallic compound and organic halogen compound. The composition cures inhomogeneously upon brushing, and the cured resin shows a yellow color.

Here reference will be made to FIGS. 1 and 2.

FIG. 1 is a data plot plotted in terms of b* vs. storage period. The values of b* were found by use of Color Computer SZ-Σ80 made by Nippon Denshoku K.K. Moreover, changes of b* with time were found by measuring ΔE with the results plotted in FIG. 2. Experimentation was then conducted with two selected factors, i.e., storage condition and storage period. The samples were placed at 60° C., 23° C. and exposed to sunlight while they were stored, and the changes of ΔE were measured just after the preparation of samples and after the passing of one, two, four, nine and thirteen weeks. The larger the positive value of b*, the stronger the yellowing of the samples. The value of ΔE represents a difference in the color of each sample between colors rendered just after preparation and after colors rendered in the lapse of time. As the ΔE value exceeds 1, the sample is visually found to vary in color. As can be seen from FIGS. 1 and 2, the sample according to Comparative Example 9 wherein the organic peroxide reacts with the aromatic tertiary amine shows a strong yellow color even just after its preparation, with the degree of yellowing increasing with time.

In FIG. 1, Curve 1 is obtained by plotting the data of the sample according to Comp. Example 9 at 60° C.; Curve 2 the sample according to Comp. Example 9 exposed to sunlight; Curve 3 the sample according to Comp. Example 9 at 23° C.; Curve 4 the sample according to Example 1 at 60° C.; Curve 5 the sample according to Example 1 exposed to sunlight; and Curve 6 the sample according to Example 1 at 23° C.

Figure 2:
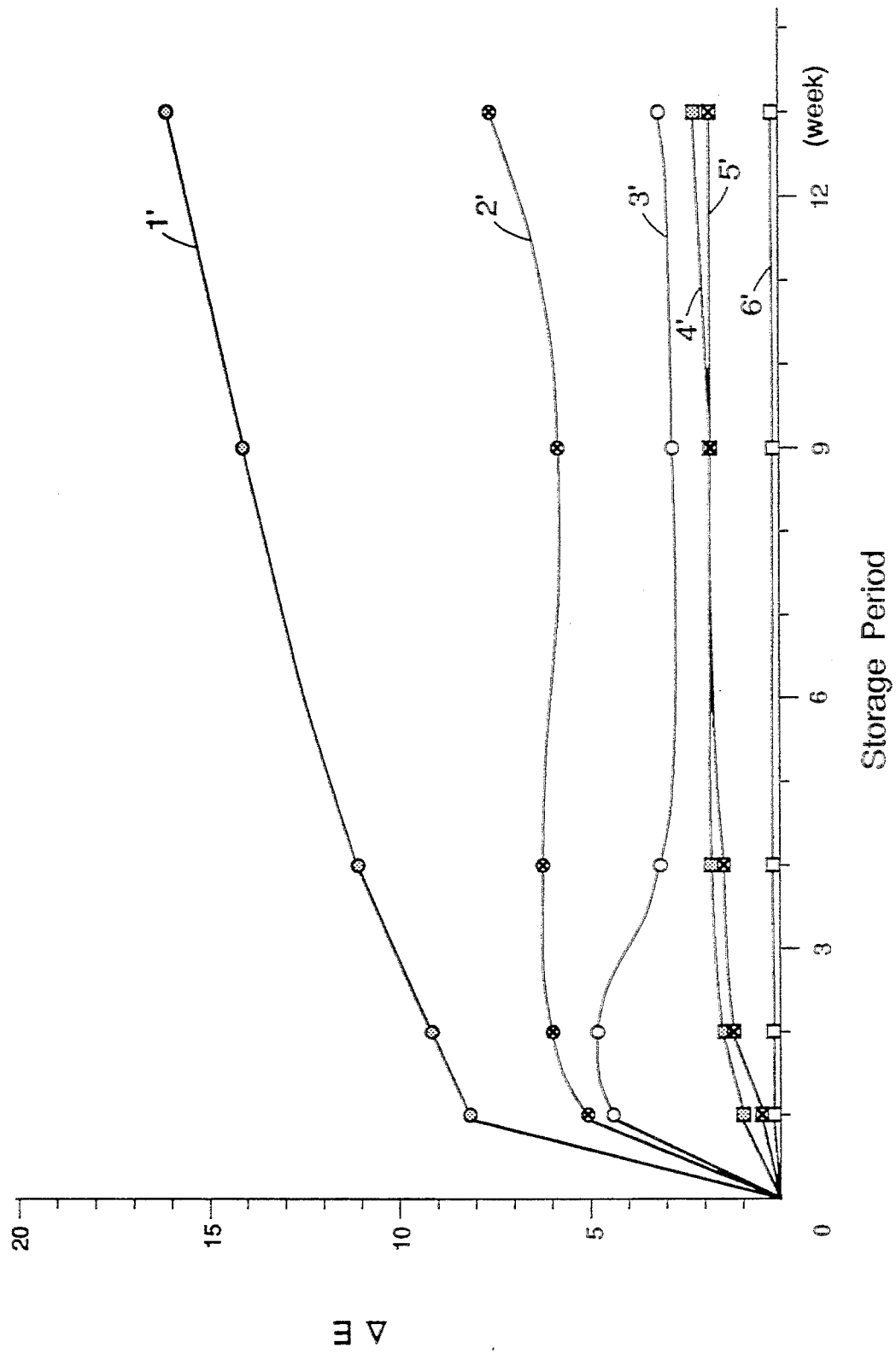
FIG. 2 represents color difference "$\Delta E$" with time.

In FIG. 2, Curve 1' is obtained by plotting the data of the sample according to Comp. Example 9 at 60° C.; Curve 2' the sample according to Comp. Example 9 exposed to sunlight; Curve 3' the sample according to Comp. Example 9 at 23° C.; Curve 4' the sample according to Example 1 at 60° C.; Curve 5' the sample according to Example 1 exposed to sunlight; and Curve 6' the sample according to Example 1 at 23° C.

TABLE 1

| | \multicolumn{9}{c}{Figures for powder and liquid components in part by weight} |
|---|---|---|---|---|---|---|---|---|---|
| | Example 1 | Example 2 | Example 3 | Example 4 | Example 5 | Example 6 | Example 7 | Example 8 | Example 9 |
| Powder component | | | | | | | | | |
| Polymethylmethacrylate | 30.0 | 30.0 | 30.0 | 30.0 | 30.0 | 30.0 | 30.0 | 30.0 | 30.0 |
| Ethyl methyl copolymer | 70.0 | 70.0 | 70.0 | 70.0 | 70.0 | 70.0 | 70.0 | 70.0 | 70.0 |
| N-cyclohexyl 5-ethyl-pyrimidinetrione | 1.0 | 0.1 | 5.0 | — | 0.5 | 1.0 | 1.0 | — | 1.0 |
| 1-benzyl 5-phenyl-pyrimidinetrione | — | — | — | 1.0 | 0.5 | — | — | 1.0 | — |
| Acetylacetone copper | 0.001 | 0.001 | 0.001 | 0.0005 | 0.05 | 0.001 | 0.001 | 0.001 | 0.001 |
| Liquid component | | | | | | | | | |
| Methylmethacrylate | 95.0 | 95.0 | 95.0 | 95.0 | 95.0 | 95.0 | 95.0 | 95.0 | 95.0 |
| Ethyleneglycol dimethacrylate | 5.0 | 5.0 | 5.0 | — | — | — | — | 2.5 | — |
| Trimethylolpropane trimethacrylate | — | — | — | 5.0 | 5.0 | 5.0 | 5.0 | 2.5 | 5.0 |
| Dilauryldimethylammonium-chloride | 0.3 | 0.3 | 0.3 | 0.3 | 0.3 | 0.1 | 5.0 | 0.3 | 0.3 |
| N,N-di($\beta$-hydroxypropyl)-p-toluidine | 2.0 | 2.0 | 2.0 | 2.0 | 2.0 | 2.0 | 2.0 | 0.1 | 5.0 |
| Butylhydroxy-toluene | 0.0075 | 0.0075 | 0.0075 | 0.0075 | 0.0075 | 0.0075 | 0.0075 | 0.0075 | 0.0075 |
| Results | | | | | | | | | |
| Homogeneity in curing upon brush on technic | None | None | None | None | None | None | None | None | None |
| Color of cured resin | Colorless transparent | Colorless transparent | Colorless transparent | Colorless transparent | Colorless transparent | Colorless transparent | Colorless transparent | Colorless transparent | Colorless transparent |
| Occurence of internal air bubbles | None | None | None | None | None | None | None | None | None |
| Vicat needle curing time powder/liquid = 2 g/1 ml | 2'45" | 3'45" | 3'30" | 4'30" | 2'30" | 4'20" | 2'45" | 3'00" | 2'30" |

TABLE 2

| | \multicolumn{9}{c}{Figures for powder and liquid components in part by weight} |
|---|---|---|---|---|---|---|---|---|---|
| | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 |
| Powder component | | | | | | | | | |
| Polymethylmethacrylate | 30.0 | 30.0 | 30.0 | 30.0 | 30.0 | 30.0 | 30.0 | 30.0 | 30.0 |
| Ethyl methyl copolymer | 70.0 | 70.0 | 70.0 | 70.0 | 70.0 | 70.0 | 70.0 | 70.0 | 70.0 |
| N-cyclohexyl 5-ethyl-pyrimidinetrione | 0.01 | 10.0 | 1.0 | — | 1.0 | 1.0 | 0.01 | 10.0 | — |
| 1-benzyl 5-phenyl-pyrimidinetrione | — | — | — | 1.0 | — | — | — | — | — |
| Acetylacetone copper | 0.001 | 0.001 | 0.0001 | 1.0 | 0.001 | 0.001 | 0.001 | 0.001 | — |
| Benzoyl peroxide | — | — | — | — | — | — | — | — | 1.0 |
| Liquid component | | | | | | | | | |
| Methylmethacrylate | 95.0 | 95.0 | 95.0 | 95.0 | 95.0 | 95.0 | 95.0 | 95.0 | 95.0 |
| Ethyleneglycol dimethacrylate | 5.0 | 5.0 | 5.0 | — | — | — | 5.0 | 5.0 | 5.0 |
| Trimethylolpropane trimethacrylate | — | — | — | 5.0 | 5.0 | 5.0 | — | — | — |
| Dilauryldimethylammonium-chloride | 0.3 | 0.3 | 0.3 | 0.3 | 0.05 | 10.0 | 0.3 | 0.3 | — |
| N,N-di($\beta$-hydroxypropyl)-p-toluidine | 2.0 | 2.0 | 2.0 | 2.0 | 2.0 | 2.0 | 0.05 | 10.0 | 2.0 |
| Butylhydroxy-toluene | 0.0075 | 0.0075 | 0.0075 | 0.0075 | 0.0075 | 0.0075 | 0.0075 | 0.0075 | 0.0075 |
| Results | | | | | | | | | |
| Homogeneity in curing upon brush on technic | None | None | None | None | None | None | None | None | None |
| Color of cured resin | Colorless transparent | White | Colorless transparent | Pale blue | Colorless transparent | Blue yellow | Colorless transparent | Whitish yellow | Yellow |
| Occurence of internal air bubbles | None | None | None | None | None | None | None | None | Occurred |
| Vicat needle curing time powder/liquid = 2 g/1 ml | 12'00" | 8'30" | 15'30" | 2'30" | 6'15" | 2'30" | 3'30" | 3'30" | 3'45" |

Some improvements are achieved by the development of a powder-liquid type of cold-polymerizing resin comprising a powder component consisting of no added benzoyl peroxide homopolymer and/or copolymer of polymethacrylate ester, a pyrimidinetrione derivative and an organometallic compound and a liquid component consisting of a radical polymerizable compound having at least one ethylenically unsaturated double bond, an organic halogen compound, an aromatic tertiary amine and a polymerization inhibitor, as mentioned just below.

IMPROVEMENT IN INHOMOGENEOUS CURING UPON BRUSH ON TECHNIC

In general, such a powder-liquid type of dental cold-polymerizing resin has been used by brush on technic. A difference in the curing time between the outer surface and central portions of a scoop of material taken up by brush on technic poses a grave problem to dentists or dental technicians. This inhomogeneous curing is successfully eliminated by use of a combination of four catalysts as contemplated in the invention, i.e., (i) the pyrimidinetrione derivative, (ii) the organometallic compound, (iii) the organic halogen compound, and (iv) the aromatic tertiary amine.

IMPROVEMENT IN THE YELLOWING OF CURED MATERIALS

When dental cold-polymerizing resin is cured by the reaction in which the pyrimidinetrione derivative, organometallic compound and organic halogen compound take part, it is known that the cured material does not suffer from yellowing. However, this fails to solve the problem in connection with inhomogeneous curing upon brush on technic. According to the invention, it is found that the addition of the aromatic tertiary amine to these catalysts provides a solution to both the problems in connection with inhomogeneous curing upon brush on technic and yellowing.

IMPROVEMENT IN THE OCCURRENCE OF INTERNAL AIR BUBBLES UPON BRUSH ON TECHNIC

When dental cold-polymerizing resin is cured by the reaction in which conventional catalysts, i.e., benzoyl peroxide in particular and an aromatic tertiary amine take part, some considerable internal air bubble are generated. This is responsible for a re-fracture, because polishing scum remains in the air bubbles in the form of impurities, or the air bubbles makes the mechanical strength of the resin inferior so that the resin fails to produce its own properties. Only by use of the four catalysts according to the invention is it possible to provide a solution to these problems, because no air bubble is generated at all even upon relying on brush on technic.

What we claim is:

1. A power liquid dental cold-polymerizing resin composition composed of powder and liquid components that are brought in contact with each other and mixed together for curing,
   and mixed together for curing,
   (A) a component selected from the group consisting of no added benzoyl peroxide homopolymer of polymethacrylate ester, no added benzoyl peroxide copolymer of polymethacrylate ester, and mixtures thereof,
   (B) a pyrimidinetrione derivative in an amount lying in the range of 0.05 to 5% by weight per 100 parts by weight of the polymer (A), and
   (C) an organometallic compound in an amount lying in the range of 0.0005 to 0.1 parts by weight per 100 parts by weight of the polymer (A), and
   said liquid component comprising:
   (D) a radical polymerizable compound having at least one ethylenically unsaturated double bond,
   (E) an organic halogen compound in an amount lying in the range of 0.1 to 5 parts by weight per 100 parts by weight of the compound (D),
   (F) an aromatic tertiary amine in an amount lying in the range of 0.1 to 5 parts by weight per 100 parts by weight of the compound (D), and
   (G) a polymerization inhibitor.

2. A dental cold-polymerizing resin composition as claimed in claim 1, wherein the pyrimidinetrione derivative is at least one member selected from the group consisting of N-cyclohexyl 5-ethylpyrimidinetrione, 1-benzyl 5-phenylpyrimidinetrione, 5-butylpyrimidinetrione, 5-phenylpyrimidinetrione, 1,3-dimethylpyrimidinetrione, and 5-ethylpyrimidinetrione.

3. A dental cold-polymerizing resin composition as claimed in claim 1, wherein the organometallic compound is at least one member selected from the group consisting of acetylacetone copper, copper 4-cyclohexylbutyrate, copper acetate, copper oleate, acetylacetone manganese, manganese naphthenate, octylic acid manganese, acetylacetone cobalt, cobalt naphthenate, acetylacetone lithium, lithium acetate, acetylacetone zinc, zinc naphthenate, acetylacetone nickel, nickel acetate, acetylacetone aluminum, acetylacetone calcium, acetylacetone chromium, acetylacetone iron, sodium naphthenate, and rare earth octoate.

4. A dental cold-polymerizing resin composition as claimed in any one of claims 1-3, wherein the radical polymerizable compound having at least one ethylenically unsaturated double bond is a monofunctional methacrylate.

5. A dental cold-polymerizing resin composition as claimed in any one of claims 1-3, wherein the radical polymerizable compound having at least one ethylenically unsaturated double bond is a monofunctional acrylate.

6. A dental cold-polymerizing resin composition as claimed in any one of claims 1-3, wherein the radical polymerizable compound having at least one ethylenically unsaturated double bond is a polyfunctional methacrylate.

7. A dental cold-polymerizing resin composition as claimed in any one of claims 1-3, wherein the radical polymerizable compound having at least one ethylenically unsaturated double bond is a polyfunctional acrylate.

8. A dental cold-polymerizing resin composition as claimed in any one of claims 1-3, wherein the organic halogen compound is at least one member selected from the group consisting of dilauryldimethylammoniumchloride, lauryldimethylbenzylammoniumchloride, tetra-n-butylammoniumchloride, trioctylmethylammoniumchloride, benzyldimethylcetylammoniumchloride, and benzyldimethylstearylammoniumchloride.

* * * * *